United States Patent [19]
Altmann et al.

[11] Patent Number: 5,601,570
[45] Date of Patent: Feb. 11, 1997

[54] STEREOTAXIC ROTATIONAL ADAPTOR

[75] Inventors: Bert L. Altmann, Long Beach; J. David Kopf, Tujunga, both of Calif.

[73] Assignee: David Kopf Instruments, Tujunga, Calif.

[21] Appl. No.: 403,296

[22] Filed: Mar. 14, 1995

[51] Int. Cl.$^6$ .................................................. A61B 19/00
[52] U.S. Cl. ........................... 606/130; 119/752; 119/712
[58] Field of Search ................... 606/130, 87, 96, 606/102, 116, 117, 163, 164, 165; 269/71, 155; 119/752, 755, 756, 712, 837, 814

[56] References Cited

U.S. PATENT DOCUMENTS

| | | | |
|---|---|---|---|
| 4,617,925 | 10/1986 | Laitinen | 606/130 |
| 4,638,798 | 1/1987 | Shelden et al. | 606/130 |
| 5,154,723 | 10/1992 | Kubota et al. | 606/130 |
| 5,330,485 | 7/1994 | Clayman et al. | 606/130 |

Primary Examiner—Robert A. Hafer
Assistant Examiner—Justine Yu
Attorney, Agent, or Firm—Bruce H. Johnsonbaugh

[57] ABSTRACT

A rotational adaptor is provided for use with a stereotaxic instrument used in brain research to hold and stabilize the head of a small animal, such as a rat, having a cradle with two ear bars and a nose clamp wherein the cradle may be rotated while maintaining support of the animal's head by the ear bars and the nose clamp. The device allows electrodes and micropipettes to be implanted through the side of the skull as well as through the top of the skull, increasing the number of available implant pathways and consequently reducing trauma experienced by the animal.

2 Claims, 4 Drawing Sheets

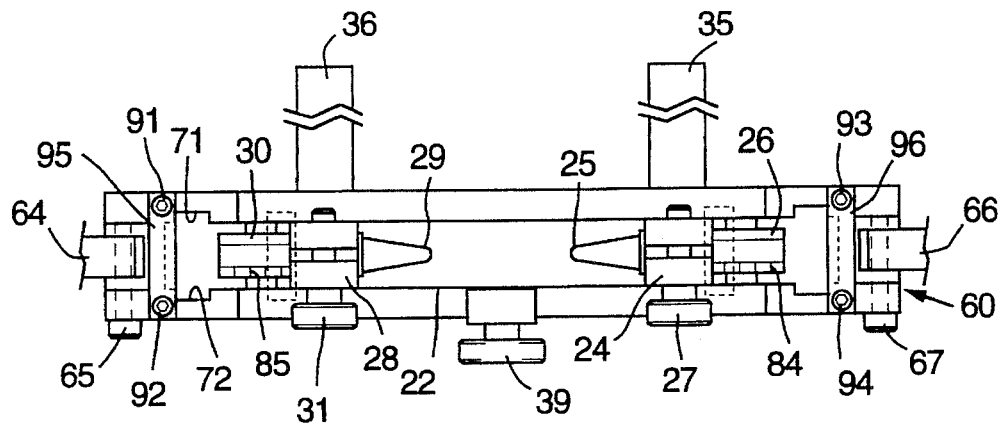
FIG. 4
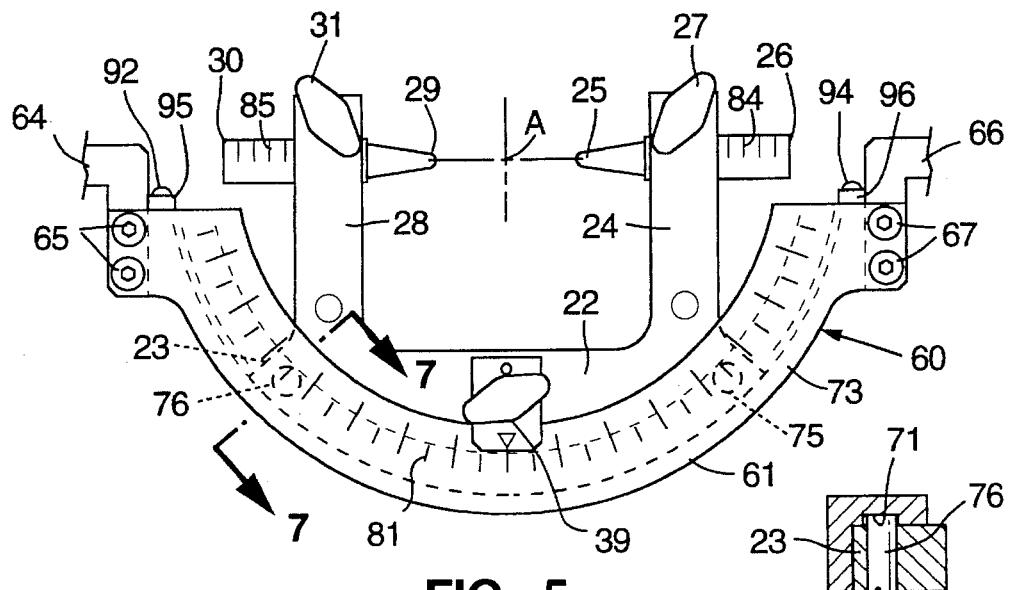
FIG. 5
FIG. 7
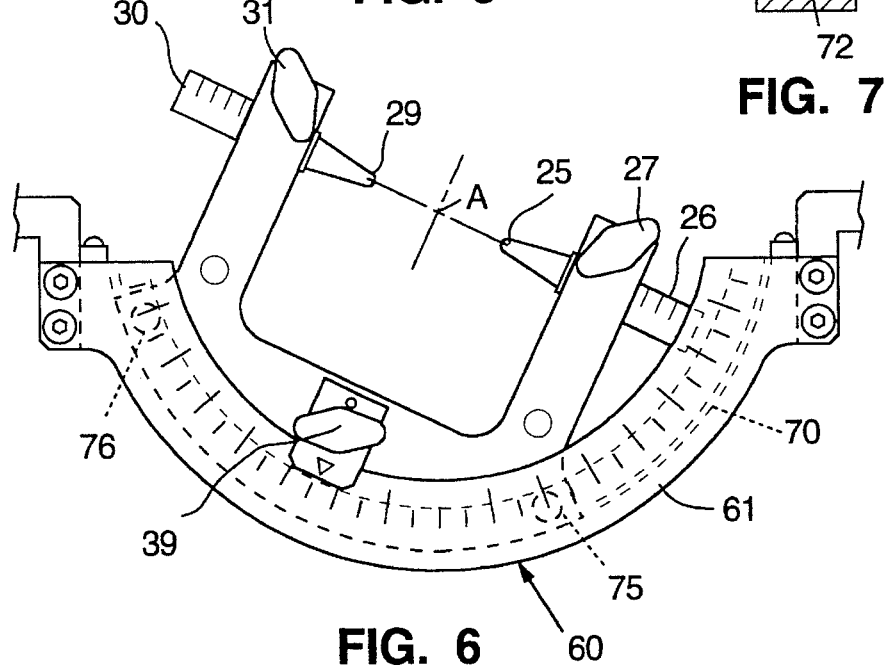
FIG. 6

STEREOTAXIC ROTATIONAL ADAPTOR

BACKGROUND

This invention pertains generally to stereotaxic instruments used in brain research. In particular, the present invention relates to a rotational adaptor which may be used in conjunction with commercially available small animal stereotaxic instruments to allow the rotation of the animal's head in the instrument.

It is known in the prior art to provide small animal stereotaxic instruments which use ear bars and a nose clamp to provide a three point support for an animal's head. It is also known in the art to provide adjustable ear bars for use in conjunction with an adjustable nose clamp to achieve a predetermined and repeatable position for supporting an animal's head for brain research. These prior art mechanisms are not rotatable. As brain research becomes more advanced and as the placement of electrodes, micropipettes and other devices requires more precision, as well as more insertion pathways, it becomes important to provides stereotaxic instruments with increasing precision and flexibility to facilitate further advances in brain research.

A further concern in the design and use of such stereotaxic instruments is to minimize or even eliminate the trauma and pain which might otherwise be experienced by the animal in question.

BRIEF SUMMARY OF THE INVENTION

According to the present invention, a rotational adaptor is provided for use with conventional small animal stereotaxic instruments for providing a three point mounting plane for the head of the animal and wherein the head of the animal may be placed in a predetermined and repeatable position. The ability to rotate the head is extremely useful for the implantation of electrodes, micropipettes or other devices wherein the shortest and safest path of placement is through the side of the skull rather than through the top of the skull.

The present invention includes a three point support for the head of a small animal which allows for rotation of the animal's head from side to side and, also, allows the rotation of the nose of the animal upward or downwardly relative to the ears of the animal.

A primary object of the present invention is to provide a mechanism which achieves a three point support for the head of a small animal and which may be rotated from side to side to allow implantation of electrodes, micropipettes and similar devices through the side of the skull as well as through the top of the skull.

A further object of the invention is to provide a rotatable stereotaxic head support for a small animal which utilizes adjustable ear bars and an adjustable nose clamp which may be rotated and which achieves a very precise and repeatable positioning of the animal's head.

Another object of the invention is to provide a rotatable stereotaxic support which significantly increases the number of pathways available for implantation of electrodes, micropipettes and other devices and which simultaneously minimizes trauma or other adverse effects upon the animal being studied.

Other objects of this invention will become apparent from the following description of the preferred embodiment and the drawings wherein

BRIEF DESCRIPTION OF THE DRAWINGS

FIG. 4 is a top view of a portion of the mechanism shown in FIGS. 1–3;

FIG. 5 is a front, elevational view of a portion of the apparatus shown in FIGS. 1–3;

FIG. 6 is a front, elevational view of the apparatus wherein a portion of the apparatus has been rotated in a clockwise direction from the position shown in FIG. 5; and FIG. 7 is a section on the line 7—7 of FIG. 5.

DETAILED DESCRIPTION OF THE INVENTION

Figure 1:
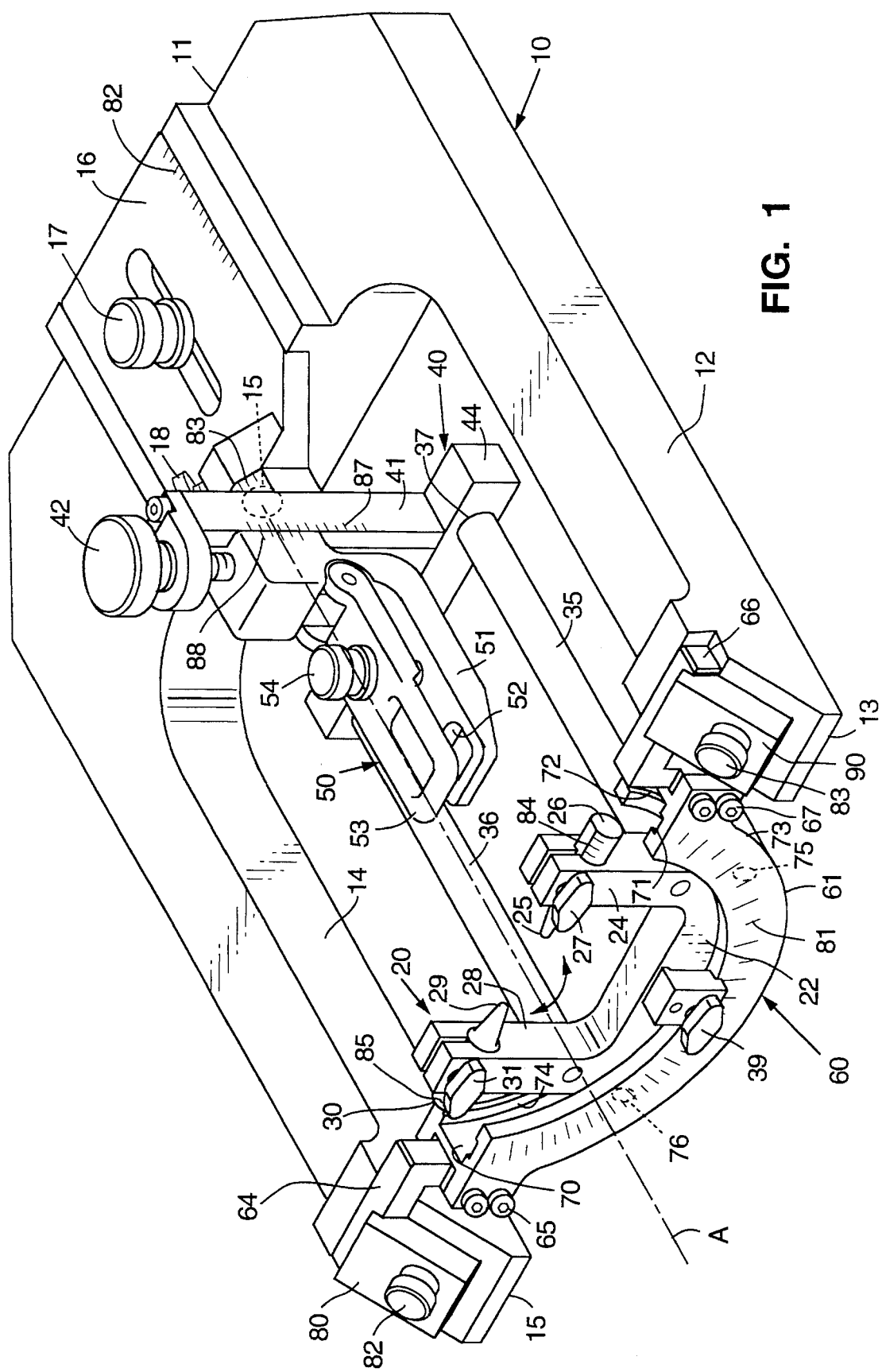
FIG. 1 is a perspective view of the rotational adaptor according to the present invention used in conjunction with a commercially available stereotaxic instrument.
Figure 2:
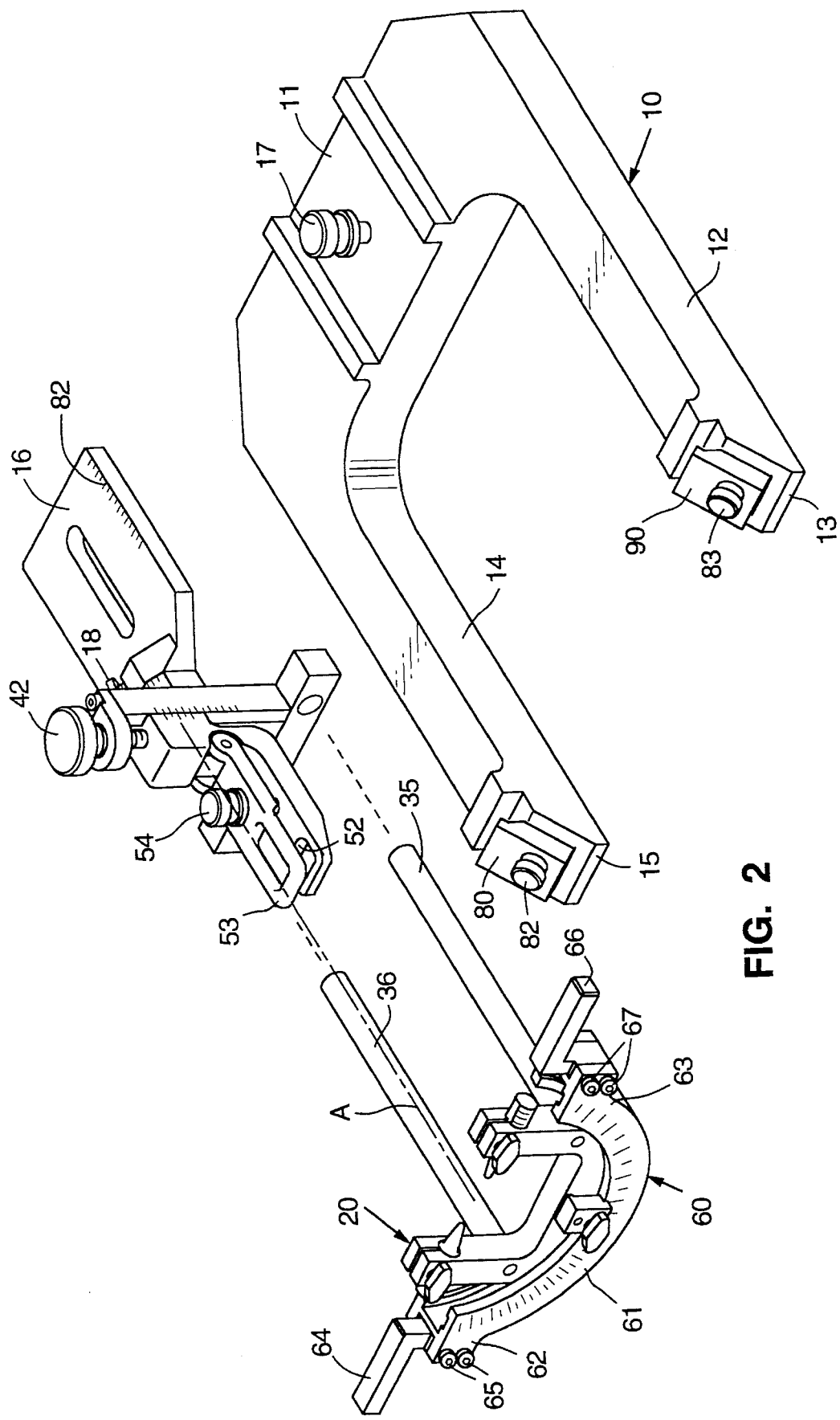
FIG. 2 is an exploded view showing the major components of the apparatus of FIG. 1.

As shown best in FIGS. 1 and 2, a generally U-shaped frame 10 is shown which is a portion of a commercially available stereotaxic instrument. The U-shaped frame 10 has a central body portion 11, a first arm 12 which extends from the body 11 and terminates in first end 13 and a second arm 14 which extends from body 11 and terminates in end 15. The U-shaped frame 10 is ordinarily elevated a suitable height from a base plate (not shown) and is typically supported from the base plate by support arms extending downwardly from arms 12 and 14.

Figure 3:
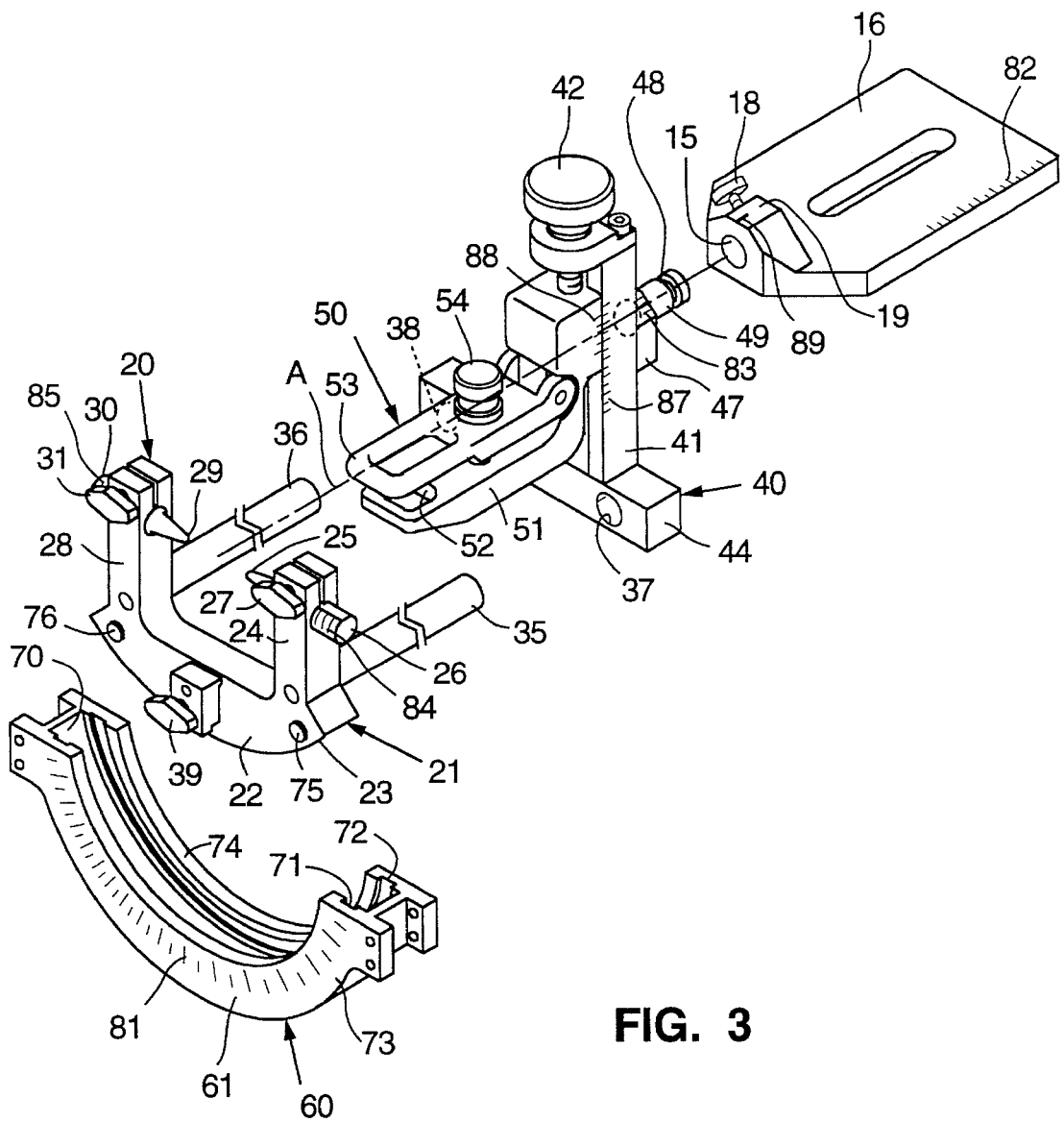
FIG. 3 is an exploded view of a portion of the mechanism shown in FIGS. 1 and 2.

A cradle means shown generally as 20 is supported by cradle support means 60. As shown best in FIG. 3, cradle means 20 includes a first section 21 for supporting the ears of a small animal, such as a rat, and a second portion shown generally as 40 for supporting the nose of the rat or other small animal.

The embodiment shown in the drawings is the preferred embodiment for use with rats and other rodents such as mice and ferrets. It is within the scope of this invention, however, to support the heads of other small animals, such as dogs, cats and monkeys, wherein some design parameters would have to be modified to accommodate the heads of those other animals.

The first section 21 of cradle means 20 includes a base section 22 having an arcuate shape and a smooth lower surface 23 which is carried by and which is free to be rotated within the cradle support means 60. The cradle base 22 supports a right ear bar support arm 24 which in turn carries a right ear bar 25. Ear bar 25 constitutes one end of a single piece bar 26, which has calibrations 84 formed thereon. Ear bar 25 is secured in a given position by thumbscrew 27. A left ear bar support arm 28 is provided which supports an adjustable left ear bar 29. The left ear bar 29 constitutes one end of a single piece bar 30, which has calibrations 85 formed thereon (FIGS. 4–6). Left ear bar 29 is held in a desired position by tightening thumbscrew 31. The tops of support bars 24 and 28 are slotted so that the thumbscrews 27 and 31 may adequately tighten the ear bars 25 and 29.

The second section 40 of the cradle means 20 includes a nose clamp support arm 41 mounted on a horizontal nose clamp support base 44 and nose clamp means shown generally as 50. The second section 40 of cradle means 20 is connected to the first section 21 by lower rods 35 and 36 which are connected to the base 22 of first section 21 and extend into passageways 37 and 38 formed in the nose clamp support base 44. Nose clamp support arm 41 carries at its Upper portion an adjustable thumbscrew 42 which is utilized to raise or lower the nose clamp means 50. Nose clamp means 50 includes a horizontally extending tooth bar 51 having an opening 52 (FIG. 2) formed near its outer end and being of sufficient size to receive the upper incisors of the rat or other small animal. A nose bar 53 is carried above the tooth bar 51. Nose bar 53 is adjustable relative to tooth bar 52 by thumb screw 54. The height of the tooth bar 51 is indicated by calibrations 87 on nose clamp support arm 41 and by calibrations 88 on the upper portion of the generally L-shaped tooth bar 51.

A cylindrical mounting pin 49 extends horizontally from nose clamp support arm 41. Mounting pin 49 extends into a cylindrical recess 15 formed in pivot support member 16 which is in turn carried by the body 11 of the U-shaped frame 10 and which is secured to the U-shaped frame 10 by thumbscrew 17. Thumbscrew 18 is carried by pivot support member 16 and seats in a recess 48 formed near the end of pin 49. The rotational position of pin 49 is indicated on scale 83 carried by member 47 attached to support arm 41. Indicator 89 formed on an elevated flat surface 19 of pivot support member 16 is used with scale 83 to note the rotational position of cradle means 20.

The cradle support means 60 comprises a crescent shaped yoke 61 having a first end 62 and a second end 63. The first end 62 is connected to an L-shaped mounting arm 64 by allen screws 65 and second end 63 is connected to L-shaped mounting bar 66 by allen screws 67. Yoke 61 has a rotational scale 81 (FIG. 3) formed thereon to indicate rotational position of cradle means 20.

Grooves 71 and 72 shown best in FIG. 7 are formed in the side walls 73 and 74 of yoke 61. Pins 75 and 76 are carried by the base member 22 of cradle means 20 and extend into grooves 71 and 72, as shown best in FIG. 7. Pins 75 and 76 support the cradle means 20 by sliding in grooves 71 and 72.

The L-shaped mounting bars 64 and 66 shown in FIG. 2 are carried by the ends 13 and 15 of U-shaped frame 10 by tabs 80 and 81 and thumb screws 82 and 83, respectively.

Plates 95 and 96 (shown only in FIGS. 4–6 for clarity) are mounted at each upper end of yoke 61 by screws 91,92 and 93,94, respectively, to prevent the pins 75 and 76 from being rotated out of grooves 71 and 72.

Referring to FIGS. 5 and 6, a brief description of the operation will be given. The head of an anesthetized animal such as a rat is placed between ear bars 25 and 29. The ear bars are loosened by thumbscrews 27 and 31 and are slid inwardly toward each other to engage the meatus of each ear and, by reference to the calibrations 84 and 85 on bars 26 and 30, the rat's skull is typically centered on axis A. Axis A extends from a point lying midway between ear bars 25 and 29 through the center of mounting pin 49. Thumbscrews 27 and 31 are tightened. Simultaneously, the rat's upper jaw is placed on tooth bar 51 with its upper incisors extending through opening 52. Nose bar 53 is moved downwardly with thumbscrew 54 to hold the forward part of the rat's skull firmly in position with the upper surface of the nose typically centered on axis A. At this point, it is possible to raise or lower the nose of the rat by adjusting thumb wheel 42 to cause rotation of the rat's skull in an upward or downward direction around the ear bars 25 and 29. Nose position is indicated by scales 87 and 88. The rotation of the rat's skull in this direction is referred to as "pitch," whereas rotation of the rat's skull from side to side is referred to as a "roll" rotation. With the rat's nose set at the proper elevation by thumbscrew 42, thumbscrew 18 is loosened and thumbscrew 39 carried by the base 22 of cradle 20 is released. The cradle 20 is now free to rotate, for example, to the position shown in FIG. 6 whereupon thumbscrew 39 is tightened which secures cradle 20 relative to cradle support means 60. Thumbscrew 18 is also tightened. The rotational position is indicated by scales 81 and 83. With the rat's skull rotated to the position indicated in FIG. 6, electrodes, micropipettes and other instruments may be inserted into the rat's brain by shorter and less threatening pathways than may otherwise be available when the rat's skull is held in a horizontal attitude shown by FIG. 5.

Using the instrument shown, it is possible to record the position of a particular rat's head for a given placement of an electrode, remove the rat from the apparatus and, at a later time, reposition the rat's head in precisely the same location. It is also possible with the present instrument to use animals, such as rats, of similar weight and age and to place their heads in the apparatus in precisely the same orientation so that the electrodes or micropipettes may be introduced with a high degree of accuracy and precision into the same target region of the brain of different rats.

The cradle means 20 provides a three point stereotaxic mounting plane for the animal's head and, when the cradle means 20 is rotated, both ear bars and the nose clamp move together in unison. This is accomplished because the first section 21 of the cradle means and the second section 40 are rigidly connected by lower rods 35 and 36. Cradle means 20 is a unitary structure which contains two adjustable ear bars and an adjustable nose clamp which may be rotated as a unit in a "roll" direction, wherein the animal's head is rotated sideways.

The attached drawings show the preferred embodiment of the invention. It is understood that variations on the design shown can be made without departing from the spirit of this invention. For example, the second section 40 of the cradle means 20 does not have to be pivotally supported on the U-frame 10. However, providing the pivotal support for the nose clamp section of the mechanism increases its stability. It is also within the scope of this invention to utilize different methods for supporting the cradle means 20 from the U-frame 10. The use of the crescent shaped yoke 61 is the preferred mechanism, but other cradle support mechanisms could be utilized so long as the cradle means 20 was free to rotate and provided that cradle means 20 can be secured in a given position of rotation such as that shown in FIG. 6.

It is also understood that it is not necessary for the skull of the animal to necessarily be centered on axis A. It is within the scope of this invention that the animal's skull may be intentionally placed off-center for certain laboratory procedures. Off-center positioning of the skull is contemplated by the invention and the adjustable ear bars 25 and 29 accomplish that type of placement.

What is claimed is:

1. A head support for use in small animal brain research rotatable about an axis A comprising:

rotatable cradle means including two ear bars and a nose clamp for providing three point support for the head of said small animal, said cradle means comprising a first section which carries said ear bars and a second section connected to said first section, said second section carrying said nose clamp, a stationary, crescent-shaped yoke means for supporting said first section of said cradle means whereby said first section of said cradle means is rotatable relative to said yoke means so that said ear bars rotate about said axis A, a stationary, pivotal support means located on axis A for supporting said second section of said cradle means, mounting means carried by said nose clamp for connection to said pivotal support means allowing said nose clamp to rotate about said axis A as said ear bars rotate about said axis A.

2. The apparatus of claim 1 further comprising:

a generally U-shaped frame, said frame having a body and first and second arms extending from said body, said stationary, pivotal support means is carried by said body of said generally U-shaped frame, and said crescent-shaped yoke means is carried by said first and second arms of said generally U-shaped frame.

* * * * *

UNITED STATES PATENT AND TRADEMARK OFFICE
CERTIFICATE OF CORRECTION

PATENT NO. :  5,601,570
DATED      :  February 11, 1997
INVENTOR(S):  Bert L. Altmann et al.

It is certified that error appears in the above-indentified patent and that said Letters Patent is hereby corrected as shown below:

At col. 3, line 42, the words "tabs 80 and 81" should be --- tabs 80 and 90 ---.

Signed and Sealed this

Thirteenth Day of May, 1997

Attest:

BRUCE LEHMAN

*Attesting Officer*     Commissioner of Patents and Trademarks